United States Patent [19]

Gusella

[11] Patent Number: 4,666,828

[45] Date of Patent: May 19, 1987

[54] TEST FOR HUNTINGTON'S DISEASE

[75] Inventor: James F. Gusella, Framingham, Mass.

[73] Assignee: The General Hospital Corporation, Boston, Mass.

[21] Appl. No.: 640,808

[22] Filed: Aug. 15, 1984

[51] Int. Cl.[4] .................. C12Q 1/68; C12N 15/00; C12P 19/34

[52] U.S. Cl. .................................... 435/6; 435/91; 435/172.3; 436/811; 935/9; 935/78

[58] Field of Search .................. 435/6, 91, 78, 172.3, 435/803; 436/63, 94, 501, 504, 811; 935/10, 19, 9; 424/1.1; 204/182.8

[56] References Cited

PUBLICATIONS

Gusella, J. F. et al. *Nature* vol. 306, Nov. 17, 1983 pp. 234–238.

Botstein, D. et al. *Am. J. Hum. Genet.* vol. 32, 1980 pp. 314–331.

Housman, D. et al. In: *Molecular Genetic Neuroscience*, (Schmitt, F. O. et al., editors), Raven Press, NY, 1982, p. 415–422.

Housman, D. et al. In: *Genetic Research Strategies For Psychobiology And Psychiatry*, (Gershon, E. S. et al., editors), Boxwood Press, CA., 1981, pp. 17–24.

Gusella, J., et al., Banbury Report 14: Recombinant DNA Applications To Human Disease, 261–265 (Sep. 1983).

Gusella et al., Banbury Report 14: *Recombinant DNA Applications to Human Disease*, Cold Spring Harbor Laboratory, Cold Spring Harbor, NY, pp. 261–265 (1983).

Gusella et al., *Cytogenetics and Cell Genetics*, 37 (1–4): 484–485 (1984).

*Primary Examiner*—Esther M. Kepplinger
*Assistant Examiner*—Jeremy Jay
*Attorney, Agent, or Firm*—Saidman, Sterne, Kessler & Goldstein

[57] ABSTRACT

A method for detecting the presence of the gene for Huntington's disease in a subject which comprises analyzing the human chromosome 4 of the subject for a DNA polymorphism, preferably a restriction fragment length polymorphism (RFLP), linked to Huntington's Disease.

10 Claims, 6 Drawing Figures

TEST FOR HUNTINGTON'S DISEASE

BACKGROUND OF THE INVENTION

Part of the work leading to this invention was made with U.S. Government funds. The U.S. Government has certain rights in this invention.

1. Field of the Invention

The invention relates to a detection test, especially a presymptomatic test, for Huntington's Disease, which uses recombinant DNA techniques in genetic linkage analysis.

2. Brief Description of the Background Art

Huntington's Disease ((H.D.) also known as Huntington's chorea) is a progressive neurodegenerative disorder with autosomal dominant inheritance. The first symptoms of Huntington's Disease usually occur in the third to fifth decade and the gene is completely penetrant. The disease is characterized by both progressive motor abnormality, typically chorea, and intellectual deterioration commonly accompanied by prominent psychiatric symptoms, including severe depression. The symptoms of Huntington's Disease result from premature neuronal cell death, which is marked in the basal ganglia. Although the prevalence of Huntington's Disease is only 5–10 in 100,000, because of its late onset most individuals have children before they realize they have inherited Huntington's Disease, and it thus significantly affects a much greater proportion of the population. In spite of numerous biochemical studies of peripheral tissues and of post-mortem brain tissue, the primary defect in Huntington's Disease has never been detected. Prior to this invention, there was no reliable method of presymptomatic or prenatal diagnosis of the disease.

A number of investigators have examined Huntington's Disease pedigrees in search of a genetic marker linked to the Huntington's Disease locus (Pericak-Vance, M.A., et al., *Adv. Neurol.* 23:59 (1979) and Volkers, W. S., et al., *Ann. Hum. Genet.* 44: 75–79 (1980)). Such studies have proved difficult because of the late age of onset of the disorder and the consequent need for a large number of individuals to be typed. Although investigations relying on classical polymorphic antigen and enzyme markers were uniformly negative, they did exclude the Huntington's Disease locus from 20% of the human genome (Pericak-Vance, supra). The lack of additional polymorphic protein markers precluded the possibility of testing remaining regions of the genome.

In recent years, the techniques for circumventing this difficulty have been developed (Housman, D. and Gusella, J., *Mol. Genet. Neurosc.* 415–424 (Raven, N.Y., 1982)). Recombinant DNA technology provides method for obtaining the requisite number of new genetic markers because it permits the monitoring of heritable differences in the sequence of genomic DNA. These DNA markers are termed restriction fragment length polymorphisms (RFLP's). They are detected as differences in the sizes of restriction fragments observed in Southern blotting experiments on human genomic DNA using cloned DNA probes free of repetitive sequences. Unlike classical expressed markers, DNA polymorphisms can be found in regions of the genome irrespective of whether they encode a protein. Probes that detect RFLP's can therefore be derived from known gene loci or from anonymous DNA segments. RFLP's appear to be present in all regions of the genome, thus making it feasible to construct a detailed human genetic linkage map and thereby localize disease genes.

It therefore appeared of great interest to investigate the possibility of using genetic linkage analysis with DNA polymorphisms to detect the H.D. disease gene.

SUMMARY OF THE INVENTION

The invention is based on the initial identification of an anonymous DNA probe from human chromosome 4 that detects two different RFLP's in a Hind III digest of human genomic DNA. This polymorphic DNA marker shows close genetic linkage to the H.D. gene in two separate families, although a different haplotype of the marker segregates with the Huntington's Disease gene in each family.

From this data, it was inferred that the Huntington's Disease locus resides on human chromosome 4.

Further investigations extended these observations to an additional family; to other restriction endonuclease digests with the same probe, e.g. EcoR I, or Bgl I; and to additional DNA fragments usable as probes.

Therefore, in combination, all of these studies have resulted, for the first time, in a general method for detecting the presence of the gene for Huntington's Disease which comprises analyzing the human chromosome 4 for a DNA polymorphism linked to Huntington's Disease.

Any of a variety of RFLP's, probes and restriction enzymes can be used.

In particular, the test is carried out by studying the heritability, in a combination of family members which allows the determination of phenotype, of one DNA polymorphism or a combination of two or more polymorphisms linked to H.D. The test can be used prenatally to screen a fetus or presymptomatically, to screen a subject at risk through his/her family history.

The invention also extends to products useful for carrying out the assay, such as DNA probes (labelled or unlabelled), kits, and the like.

DEFINITIONS AND TECHNOLOGICAL BACKGROUND

A number of terms and expressions are used throughout the specification and claims. In order to assure uniformity and avoid ambiguity the following definitions are provided (See also Housman, D. and Gusella, J., *Genetic Research Strategies for Psychology and Psychiatry*, p. 17, E. S. Gershon et al., editors, The Boxwood Press, 1981):

Restriction Endonuclease

A restriction endonuclease (also restriction enzyme) is an enzyme that has the capacity to recognize a specific base sequence (usually 4, 5, or 6 base pairs in length) in a double-stranded DNA molecule, and to cleave both strands of the DNA molecule at every place where this sequence appears. For example, EcoR I recognizes the base sequence GAATTC/CTTAAG.

Restriction Fragment

Figure 1:
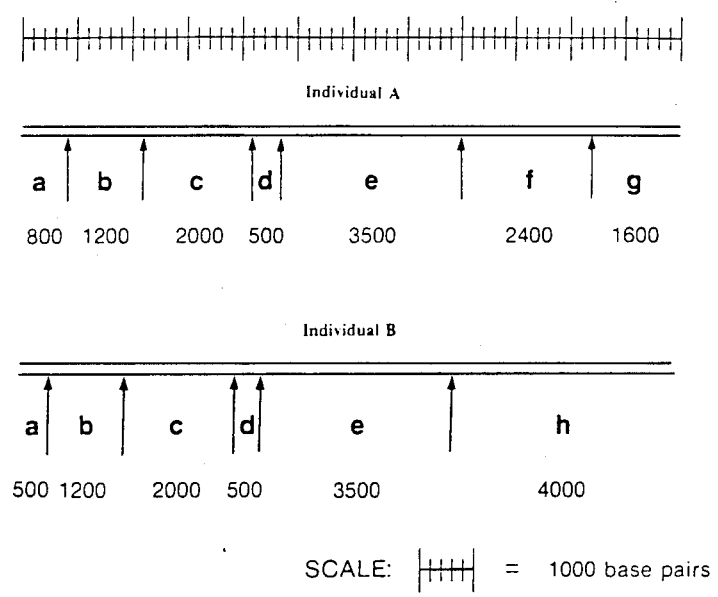
FIG. 1 shows a hypothetical restriction map from one small region of the genomes for two individuals using EcoR I as the enzyme. Each double line represents a double-stranded DNA molecule. Arrows indicate sites in the DNA where the base sequence GAATTC occurs. The DNA is digested enzymatically with the restriction enzyme EcoR I to yield fragments of the indicated sizes. Note that since individual B lacks recognition site #6, fragments f and g are not produced by digestion of the DNA of individual B with EcoR I. A larger fragment h is produced instead by the digestion of the DNA of individual B. The length of this fragment, 4,000 base pairs, is equal to the sum of lengths of fragments f and g produced by the digestion of the DNA of individual A.

The DNA molecules produced by digestion with a restriction endonuclease are referred to as restriction fragments. Any given genome will be digested by a particular restriction endonuclease into a discrete set of restriction fragments. In the hypothetical example shown in FIG. 1 (upper), the digestion of the DNA molecule gives a total of seven restriction fragments since the recognition sequence GAATTC/CTTAAG appears six times in the linear double-stranded DNA molecule. In FIG. 1 (lower), only six fragments are produced since the recognition sequence appears only five times in the DNA molecule.

Restriction Fragment Length Polymorphism (RFLP)

The genomic DNA of two individuals in a population will differ in sequence at many sites. When these differences occur in the recognition site for a restriction endonuclease, then a polymorphism in the length of restriction fragments produced by digestion of the DNA of the two individuals will result. In FIG. 1, the hypothetical pattern of restriction fragments produced by digestion of A and B with restriction enzyme EcoR I exhibits a polymorphism, since the DNA of individual A yields two fragments f and g of lengths 1,600 base pairs and 2,400 base pairs, while DNA of individual B does not yield EcoR I fragments of this size after digestion with EcoR I, but instead gives a single fragment h of length 4,000 base pairs.

Agarose Gel Electrophoresis

Figure 2:
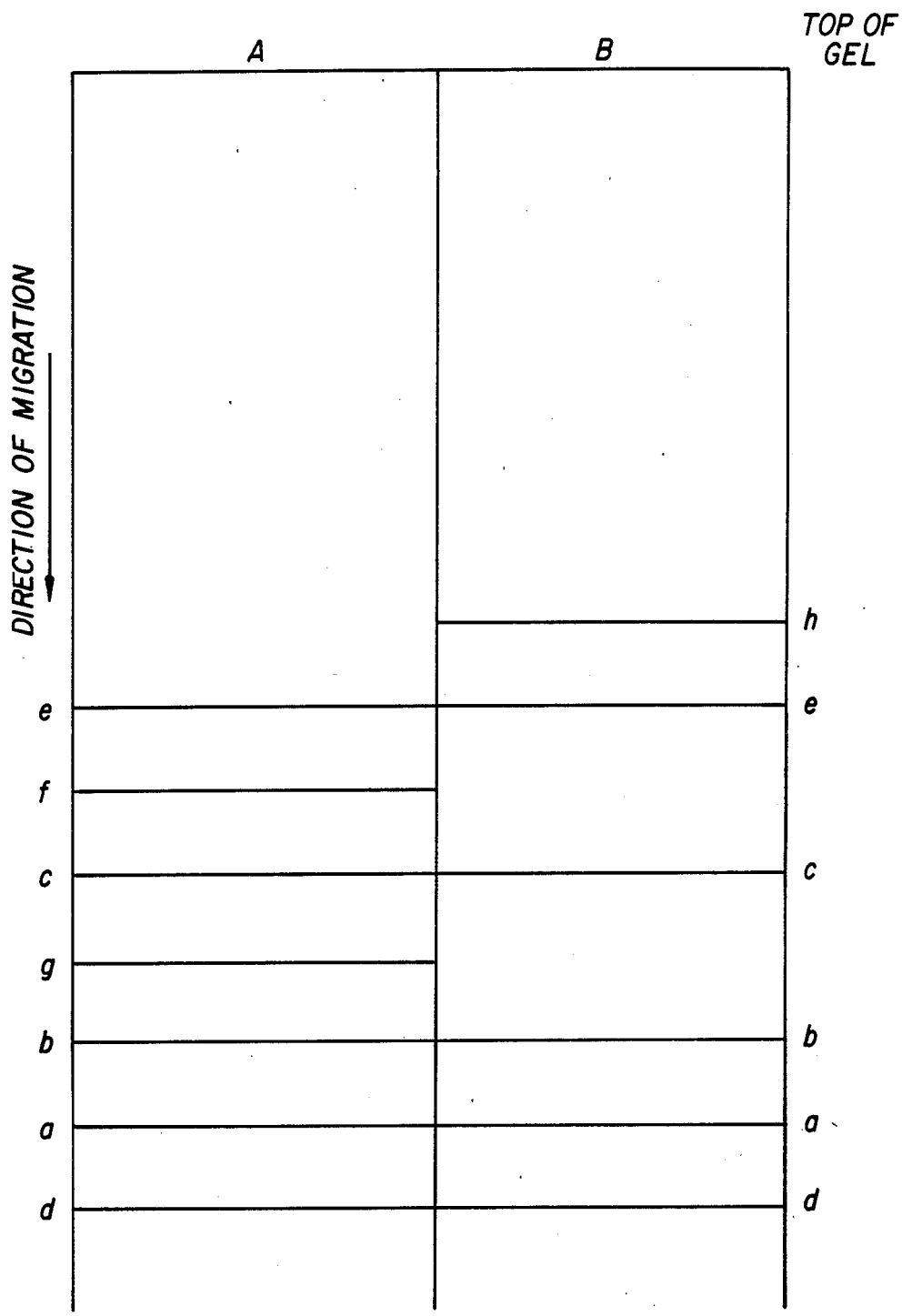
FIG. 2 shows a schematic hypothetical drawing of the result of agarose gel electrophoresis of DNA molecules obtained from the restriction digest of FIG. 1. This figure clearly illustrates the concept of an RFLP.

To detect a polymorphism in the length of restriction fragments, an analytical method for fractioning double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. In the schematic diagram shown in FIG. 2, the hypothetical restriction fragments produced by digestion with EcoR I in FIG. 1 are fractionated by agarose gel electrophoresis. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes such as those shown in hypothetical FIGS. 1 and 2 can be visualized successfully. However, most genomes, including the human genome, contain far too many DNA sequences to produce a simple pattern of restriction fragments. For example, the human genome is digested into approximately 1,000,000 different DNA fragments by EcoR I. In order to visualize a small subset of these fragments, a methodology referred to as the Southern hybridization procedure can be applied.

Southern Transfer Procedure

The purpose of the Southern transfer procedure (also referred to as blotting) is to transfer physically DNA fractionated by agarose gel electrophoresis onto a nitrocellulose filter paper while retaining the relative positions of DNA fragments resulting from the fractionation procedure. The methodology used to accomplish the transfer from agarose gel to nitrocellulose is to draw the DNA from the gel into the nitrocellulose paper by capillary action.

Nucleic Acid Hybridization

Nucleic acid hybridization is a technique which has been used in a wide variety of contexts in molecular biology since the basic principles governing reassociation of complementary nucleic acid molecules were discovered during the 1960s. Nucleic acid hybridization depends on the principle that two single-stranded nucleic acid molecules that have complementary base sequences will reform the thermodynamically favored double-stranded structure if they are mixed in solution under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe

To visualize a particular DNA sequence in the Southern hybridization procedure, a labelled DNA molecule or hybridization probe is reacted to the fractionated DNA bound to the nitrocellulose filter. The areas on the filter that carry DNA sequences complementary to the labelled DNA probe becomes labelled themselves as a consequence of the reannealing reaction. The areas of the filter that exhibit such labelling are visualized. The hybridization probe is generally produced by molecular cloning of a specific DNA sequence from the human genome.

DESCRIPTION OF THE PREFERRED EMBODIMENTS

At its broadest, the invention comprises detecting the presence of the gene for Huntington's Disease by analyzing human chromosome 4 for a DNA polymorphism linked to Huntington's Disease.

The use of RFLP's is only one preferred embodiment of detecting the polymorphism. Since, ultimately, the use of RFLP depends on polymorphisms in DNA restriction sites along the nucleic acid molecule, other methods of detecting the polymorphism can also be used. Any method of analysis which yields the linkage results using any polymorphism can be utilized. Techniques such as direct location of the polymorphism on chromosome 4 by radiolabelling, fluorescent labelling or enzyme labelling can also be utilized.

The most common methodology at present is to carry out restriction analysis using a given enzyme, perform a Southern hybridization procedure with the desired probe and identify a given RFLP or RFLP's.

In order to establish the genetic linkage or connection between the desired polymorphism and the H.D. gene, it is necessary to analyze a combination of familial relatives of the subject under investigation. The combination is chosen so that it will allow determination of the Huntington's Disease phenotype linked to the presence of the polymorphism. Thus, preferably, several individuals are examined. These may include an unaffected parent, an affected parent, an affected sibling, an unaffected sibling, as well as other, perhaps more distant, members. Ideally, an unaffected parent, an affected parent and an affected sibling should be utilized. If an affected parent is deceased, satisfactory results can still be obtained if unambiguous segregation of the polymorphism with the H.D. gene can be demonstrated in other members.

For analysis using RFLP's, blood is obtained from all individuals being studied, including the subject. DNA is extracted from lymphocytes and digested with a given restriction endonuclease. Alternatively, several digests can also be obtained. After the digest is obtained, and the same is separated by a standard technique such as, for example, agarose gel electrophoresis, the separated bands are probed with a DNA fragment coding for the RFLP sequence. There may be an optimum combination of restriction enzyme and probe. For example, in the hereinafter described G8 probe, restriction enzymes such as Hind III and EcoR I can be utilized. It is preferred to use a combination of enzymes, since it increases the information significantly. Additional enzymes that can be used with the G8 probe are Nci I, Bgl I and Pst I. Other probes can be used and combinations of probes can also be used.

The probes are labelled by standard labelling techniques such as with a radiolabel, enzyme label, fluorescent label, biotin-avidin label, and the like, and, after hybridization, are detected. Comparison of the RFLP or RFLP's for affected and unaffected individuals in the family line of the subject, with the RFLP or RFLP's for the subject under investigation will quickly reveal the presence of absence of the H.D. gene in the subject. The results are best expressed in terms of probability of presence of the H.D. gene in the subject.

Preferably, more than one polymorphism (i.e., more than one probe) is utilized for the detection. Ideally, a different polymorphism on either side of the H.D. gene will increase the sensitivity significantly.

Although the work described hereinafter is specifically addressed to the G8 probe other genetic sequences useful for probes can readily be obtained. For example, methods for generating additional new DNA fragments also linked with the H.D. gene are as follows.

A first method is to test randomly chosen pieces of human (either genomic or cDNA clones) DNA fragments that map to the appropriate region of chromosome 4. Such mapping can be achieved by three techniques:
(a) hybridization to DNA from a panel of somatic cell hybrids (see Gusella, et al., *Proceedings of the National Academy of Sciences, U.S.A.* 76:5239–5243 (1979), herein incorporated by reference);
(b) in situ hybridization to metaphase chromosome spreads; or
(c) genetic linkage to G8, H.D., raf oncogene or any other marker as already mapped to the region.

For methods (a) and (b), the new fragment need not be polymorphic, but for (c), polymorphisms must first be identified by comparing the restriction pattern of the genomic DNA at the new site in unrelated individuals. In methods (a) or (b), the mapped fragment must still be shown to detect a polymorphism in human DNA. The polymorphism which represents a new genetic marker can then be tested for linkage for H.D. in family studies as in this application, or can be tested for linkage to other DNA probes, such as G8 which are already linked to H.D.

A second, more efficient, method to generate additional DNA probes is to make a recombinant DNA library somatic cell hybrid line in which chromosome 4 or a piece of it is either one of a few or the only human chromosome present in a cell where all other chromosomes are from another species (usually mouse, hamster or rat). Recombinant clones containing human DNA are then identified by hybridization to species-specific repetitive sequences (see, for example, Gusella, et al., *Proceedings of the National Academy of Sciences, U.S.A.* 77:2829–2833 (1980), herein incorporated by reference). If the hybrid cell contains only chromosome 4, clones containing human DNA must contain DNA from chromosome 4. If other human material is present in the hybrid, then one must additionally resort to one of the mapping methods outlined in the previous paragraph.

A third method for obtaining DNA clones from chromosome 4 is to construct a library from human DNA isolated from metaphase chromosomes that have been sorted on a fluorescence activated sorter. This method can sometimes yield purified chromosomes of 95% or greater purity.

A final method of obtaining new DNA probes from the H.D. region is to use any probes already mapped to the region in order to "fish out" adjacent overlapping pieces of DNA from genomic libraries (commonly called "chromosome walking"). In this case, the primary probe mapped to chromosome 4 need not be polymorphic.

In all the cases outlined above, a probe must ultimately be found to detect a polymorphism if it is to be useful for testing H.D. The polymorphism must be found to be linked to H.D. or to other useful markers in family studies, or to be immediately adjacent to preexisting markers.

The particular polymorphism probe can be of any desired sequence length as long as it is capable of identifying the polymorphism in the involved DNA region or locus. It can be a DNA fragment by itself, or be present in longer genetic sequences or fragments, or even in a plasmid or other appropriate vehicle. Labelling and hybridization conditions can be readily determined by those of skill in the art. Usually, the stringency is standard for unique sequence DNA from within the species.

The test can be carried out prenatally or, in young or adult individuals, presymptomatically.

The method lends itself readily to the formulation of kits which can be utilized in diagnosis. Such a kit would comprise a carrier being compartmentalized to receive in close confinement one or more containers wherein a first container may contain DNA containing coding sequences for a given polymorphism, e.g. an RFLP. A second container may contain a different set of sequences coding for a second RFLP, and so on. Other containers may contain reagents useful in the localization of the labelled probes, such as enzyme substrates. Still other containers may contain restriction enzymes, buffers, and the like.

Having now generally described the invention, the same will be understood by means of specific examples which are, however, not intended to be limiting unless otherwise specified.

EXAMPLE 1

Discovery of Linkage Between Probe G8 and the H.D. Gene

This example is also described in an article by Gusella, et al., in 306 Nature 234-238 (1983), herein incorporated by reference.

Huntington's Disease Families

Figure 3:
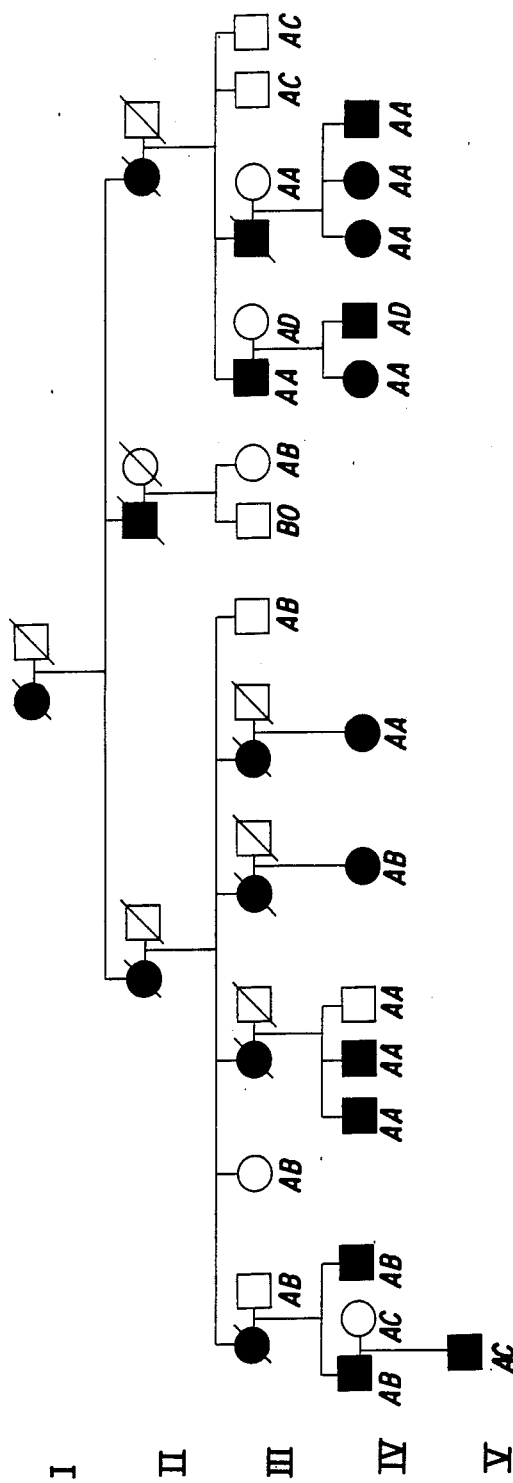
FIG. 3 shows a real pedigree of an American Huntington's Disease family. Symbols: circles, females; squares, males; a black symbol indicates that an individual is affected with Huntington's Disease; a slashed symbol indicates that an individual is deceased. This pedigree was identified through the National Research Roster for Huntington's Disease Patients and Families at Indiana University. Relevant family members were examined by a neurologist and blood samples were obtained. EBV-transformed lymphoblastoid cell lines were established for the individuals whose genotypes are shown and have been stored at the Human Genetic Mutant Cell Repository, Camden, N.J. Phenotypes at the G8 locus shown under each symbol were determined by Southern blotting as outlined in FIG. 5.
Figure 4:
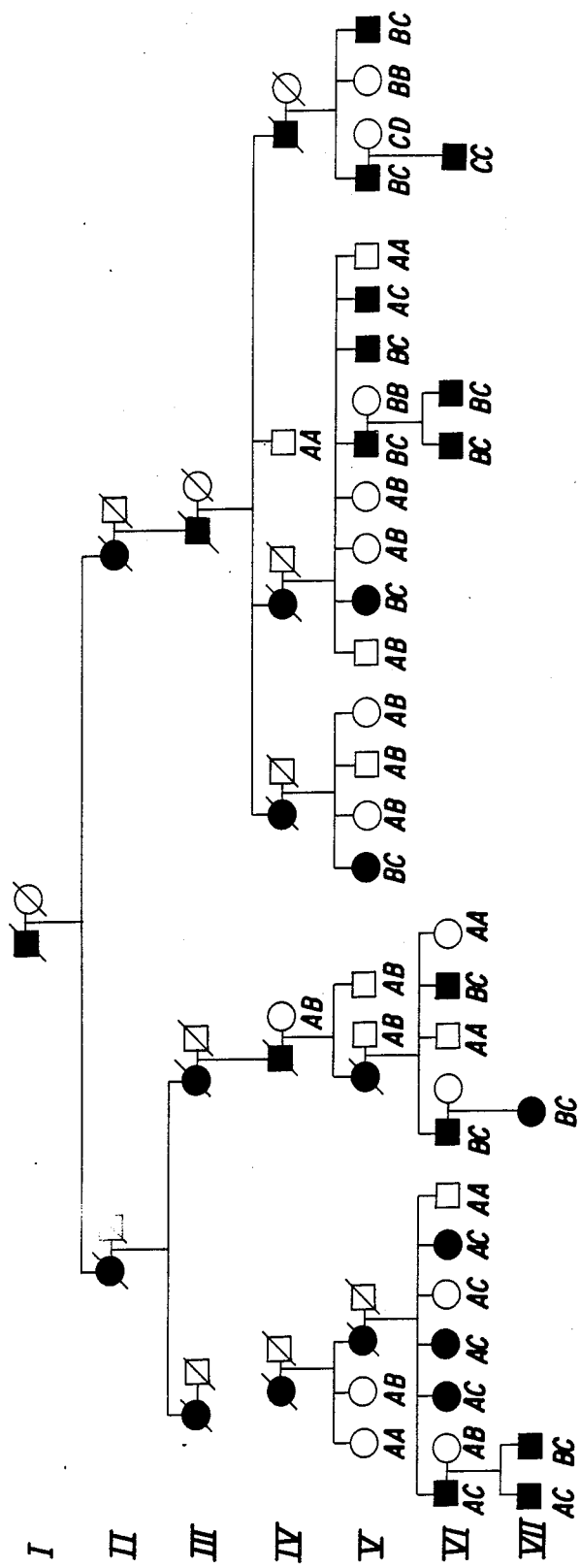
FIG. 4 shows a pedigree of a Venezuelan Huntington's Disease family. This pedigree represents a small part of a much larger pedigree. Permanent EBV-transformed lymphoblastoid cell lines were established from blood samples of these individuals. DNA prepared from the lymphoblastoid lines was used to determine the phenotype of each individual at the G8 locus as described in FIG. 3. Because of the high frequency of the Huntington's disease gene in this population, some of the spouses of affected individuals have also descended from identified Huntington's Disease gene carriers. In none of these cases, however, was the unaffected individual at significantly greater risk for Huntington's Disease than a member of the general population. Although a number of younger at-risk individuals were also analysed as part of this study, for the sake of these family members the data are not shown due to their predictive nature.

An American family of reasonable size was initially selected (FIG. 3) and blood samples were obtained to establish permanent Epstein-Barr virus (EBV)-transformed lymphoblastoid cell lines. Subsequently, a substantially larger Huntington's Disease family was located (FIG. 4). This pedigree stems from a unique community of interrelated Huntington's disease gene carriers living along the shores of Lake Maracaibo, Venezuela. In a pedigree numbering over 3,000 since the early 1800's, all Huntington's Disease patients have inherited the defective gene from a common ancestor. This is the largest known concentration of Huntington's Disease in one family. For the past three years, an expedition has spent one month annually in Venezuela collecting pedigree information, tissue samples, and clinical data. Permanent lymphoblastoid cell lines were again established for each individual to act as a permanent source of genomic DNA. In both families, each individual was examined by at least one neurologist experienced and knowledgeable about Huntington's Disease. In Venezuela, many family members were examined for three consecutive years. Individuals were diagnosed as having Huntington's Disease on the basis of family history, abnormal motor function and intellectual impairment. Each was assigned to a functional stage reflecting physical and social functioning according to a scale developed by Shoulson and Fahn, Neurology 29: 1-3 (1979). Blood samples from members of both pedigrees were analysed using at least 20 red cell and plasma markers to exclude cases of non-paternity.

Characterization of Bacteriophage Clone G8

A number of DNA probes that generally detect RFLP's have been previously identified. Some of these probes represent DNA sequences from known gene loci while others are anonymous DNA segments chosen because they contain no repetitive DNA sequences. In an initial screen for linkage to the Huntington's Disease gene, 12 such DNA markers were tested in the American family depicted in FIG. 3. Of these markers only one, G8, gave a suggestion of linkage to the Huntington's Disease gene.

The G8 clone is a recombinant bacteriophage from the human gene library of Maniatis and co-workers (Lawn et al., Cell 15: 1157-1174 (1978)). It contains 17.6 kilobases (kb) of human DNA free of repetitive sequences. In previous studies, G8 DNA was used as a probe in Southern blotting experiments in an attempt to identify RFLP's. The probe detected two invariant and several variable Hind III fragments in human genomic DNA. The probe is present in bacteriophage Charon 4A deposited at the ATCC prior to the filing of this application, and assigned thereby Accession No. 40133. The G8-containing bacteriophage can be replicated easily in an E. coli host such as E. coli LE 392, ATCC 33572. The pattern of hybridization of G8 to Hind III digested DNAs from members of the two families is shown in FIG. 5.

DNA was prepared from lymphoblastoid cell lines derived from member of two nuclear families. 5 $\mu$g of each DNA was digested to completion with 20 units of Hind III in a volume of 30 $\mu$l using the buffer recommended by the supplier. The DNAs were fractionated on a 1% horizontal agarose gel in TBE buffer (89 mM Tris, pH 8, 89 mM Na borate, 2 mM Na EDTA) for 18 h. Hind III-digested lambda-cI 857 DNA was loaded in a separate lane as a size marker. The gels were stained with ethidium bromide (0.5 $\mu$g ml$^{-1}$) for 30 min and the DNA was visualized with UV light. The gels were incubated for 45 min in 1 M NaOH with gentle shaking and for two successive 20 min periods in 1 M Tris, pH 7.6, 1.5 M NaCl. DNA from the gel was transferred in 20$\times$SSC (3M NaCl, 0.3 M Na citrate) by capillary action to a positively charged nylon membrane. After overnight transfer, agarose clinging to the filters was removed by washing in 3$\times$SSC and the filters were air dried and baked for 2 h under vacuum at 80° C. Baked filters were prehybridized in 500 ml 6$\times$SSC, 1$\times$Denhardt's solution (0.02% bovine serum albumin, 0.02% polyvinyl pyrolidone, 0.02% Ficoll), 0.3% SDS and 100 μg ml$^{-1}$ denatured salmon sperm DNA at 65° C. for 18 h. Prehybridized filters were washed extensively at room temperature in 3×SSC until no evidence of SDS remained. Excess liquid was removed from the filters by blotting on 1×Denhardt's solution, 0.1% SDS, 100 μg ml$^{-1}$ denatured salmon sperm DNA) containing approximately 5×10$^6$ c.p.m. of nick-translated G8 DNA (specific activity approximately 2×10$^8$ c.p.m. g$^{-1}$) was added to each bag which was then sealed and placed at 65° C. for 24-48 h. Filters were removed from the bags and washed at 65° C. for 30 min each in 3×SSC, 2×SSC, 1×SSC and 0.3×SSC. The filters were dried and exposed to X-ray film (Kodak XR-5) at −70°0 C. with a Dupont Cronex intensifying screen for 1 to 4 days. The haplotypes observed in each individual were determined from the alleles seen for each Hind III RFLP (site 1 and 2) as explained in FIG. 6.

Figure 5:
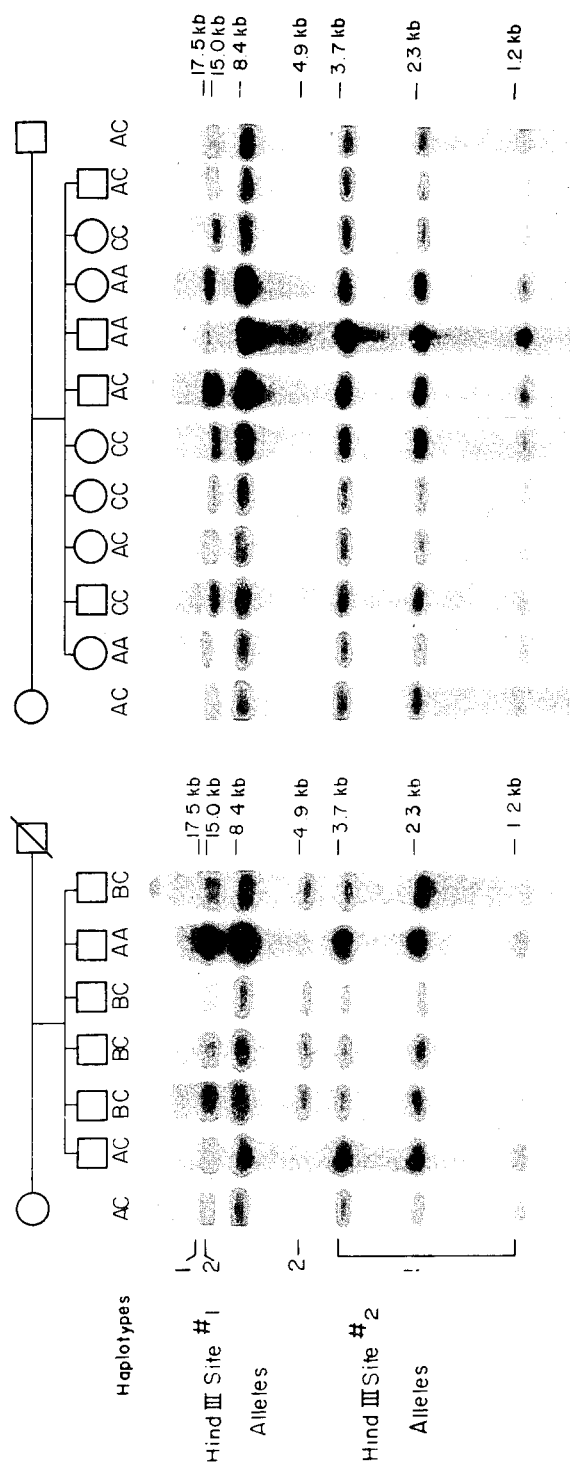
FIG. 5 shows the hybridization of the G8 probe to Hind III-digested human genomic DNA. Explanation can be found in Example 1.

The invariant Hind III fragments are seen at 8.4 kb and 2.3 kb in FIG. 5. Other fragments whose presence varied from individual to individual (in these and other unrelated individuals not shown in the figure) are seen at 17.5 kb, 15 kb, 4.9 kb, 3.7 kb and 1.2 kb. In order to determine the basis for this variation, a restriction map of clone G8 was constructed.

In initial attempts to derive this map, it was determined that the G8 insert contained five EcoR I fragments of 6.0 kb, 5.5 kb, 2.4 kb, 2.2kb and 1.5 kb. Each of these EcoR I fragments was subcloned into a plasmid vector (pBR322 or pUC9). Hind III sites within each EcoR I fragment were mapped by direct digestion of the subcloned DNA with Hind III. The order of the EcoR I fragments within the bacteriophage clone was determined by using each subclone as a probe against single or double Hind III and EcoR I digests of G8 DNA.

Variation at one Hind III site, called site 1, occurs outside of the actual cloned sequence on G8. It is detected in Southern blot experiments by hybridization to sequences at the left end of the map shown in FIG. 6. When this Hind III site is present, a 15 kb fragment is seen; when it is absent a 17.5 kb fragment is seen. The second Hind III RFLP results from the presence or absence of a site, called site 2, within the G8 insert. When this site is present, two fragments are seen, 3.7 kb and 1.2 kb, but in its absence, only a single fragment of 4.9 kb is detected.

Figure 6:
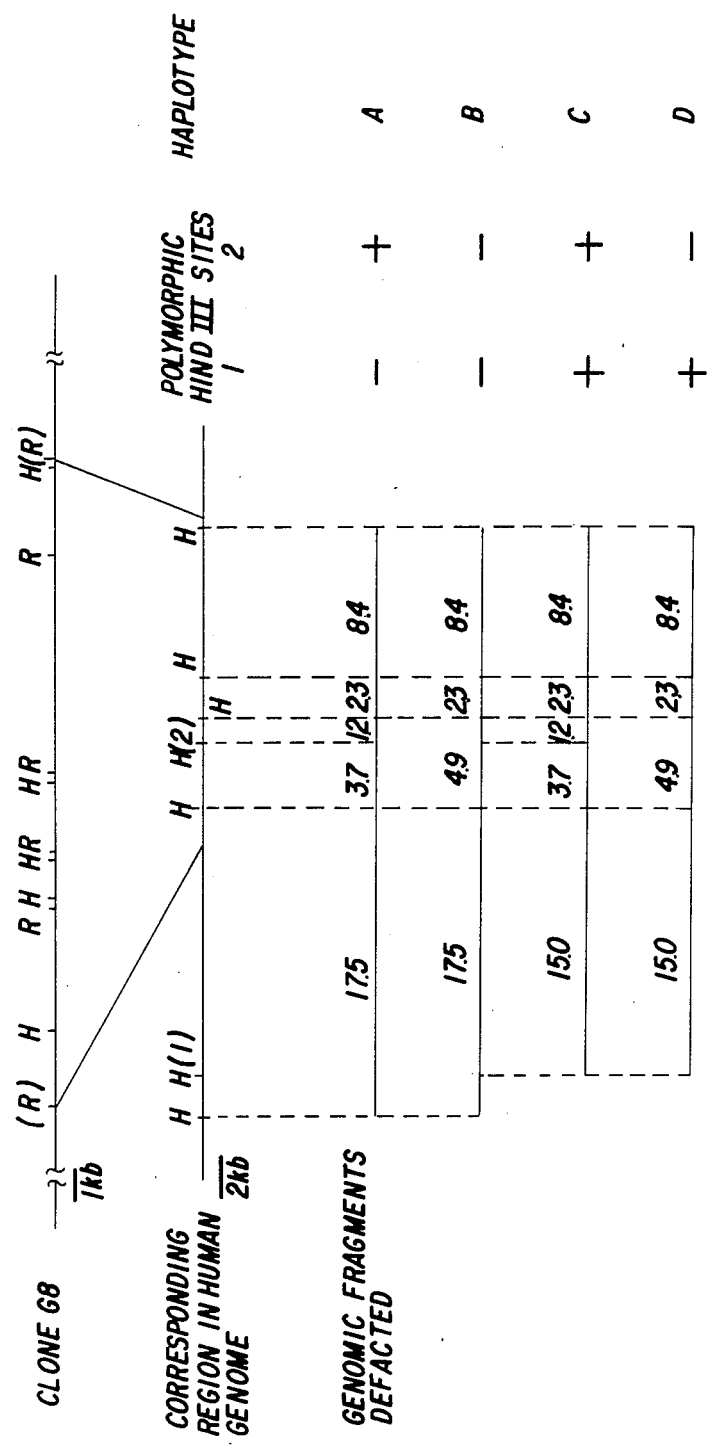
FIG. 6 shows the restriction map of the G8 insert and the corresponding region of chromosome 4. The restriction maps of the G8 insert and corresponding region of the genomic DNA were determined as described in the text.

A survey of 23 unrelated North Americans gave allele frequencies for Hind III site 1, occurring outside the clone, of 0.74 for the absence of the site, and 0.26 for the presence of the site. For Hind III site 2, mapping within the G8 clone, allele frequencies were 0.81 for the presence of the site and 0.19 for the absence of the site. In each case, the more frequent is termed allele 1, and the minor one allele 2 (see FIG. 5). Alterations in restriction fragment length due to the presence or absence of each of these sites display a Mendelian pattern of inheritance. Each EcoR I subclone was also used as a probe against Hind III digests of genomic DNA. The restriction map of the insert in G8 and the corresponding genomic region including the positions of the two variable Hind III sites is shown in FIG. 6.

This figure shows a restriction map of the G8 insert and the corresponding region of chromosome 4. The restriction maps of the G8 insert and corresponding region of the genomic DNA were determined as described in the text (H, Hind III sites; R, EcoR I sites). The polymorphic Hind III sites 1 and 2 are labelled H*(1) and H*(2). The two EcoR I sites bordering the insert are placed in parentheses as they were created during the cloning procedure and are not present in genomic DNA. Restriction sites in the Charon 4A vector arms are not shown.

When polymorphic sites in the DNA are in such close proximity that the frequency of recombination between them is negligible, they are inherited together as a unit. The combined information from both sites on a given chromosome can then be considered as a single haplotype. At the G8 locus, the two polymorphic Hind III sites are separated by only 18.7 kb. Family studies were carried out using members of the Venezuela pedigree heterozygous at both sites to test for co-segregation of the two RFLP's. The data were analysed using the computer program LIPED (Am. J. Hum. Genet. 26: 588-597 (1974)). A lod score of 4.53 was obtained at a recombination fraction (θ) of 0.0. No crossovers were seen between the two sites, supporting the hypothesis that the RFLP's are inherited together as a haplotype. The four possible combinations of alleles at site 1 and site 2 have been termed haplotypes A, B, C and D as explained for FIG. 6.

The genomic fragments generated by Hind III digestion that are detected by hybridization to the G8 probe are shown for each haplotype. The major allele due to polymorphism at the Hind III site 1 is 17.5 kb fragment resulting from the absence of cleavage (−). The minor allele, as 15.0 kb fragment, results from the presence of cleavage (+) at this site. The major allele due to polymorphism at Hind III site 2 occurs when the site is present (+), yielding fragments of 3.7 and 1.2 kb. The minor allele in this case is a 4.9 fragment occurring when site 2 is absent (−). The haplotypes were named as follows: A, major allele at site 1, major allele at site 2; B, major allele at site 1, minor allele at site 2; C, minor allele at site 1, major allele at site 2; D, minor allele at site 1, minor allele at site 2. It should be noted that the gel pattern for the combination AD is identical to that for BC. These can only be distinguished if the linkage phase of the alleles at sites 1 and 2 is determined by typing immediate relatives of the individual in question.

If no linkage disequilibrium exists between the two polymorphic Hind III sites then the frequency of these haplotypes in the population will be 0.61, 0.14, 0.20, and 0.05 respectively. These frequencies are predicted from the allele frequencies at each polymorphic Hind III site. In the limited sample of 23 individuals, frequencies were observed for A, B, C and D of 0.64, 0.11, 0.22 and 0.04 indicating that there is not a high degree of disequilibrium in the general North American population between these two RFLP's. A much larger sample of unrelated individuals will be necessary to determine with certainty whether any significant degree of disequilibrium exists. The predicted level of heterozygosity at the G8 locus if the two sites are in equilibrium is 57%, making this an excellent genetic marker.

Mapping of G8 to Chromosome 4

The G8 sequence was mapped to a human chromosome by Southern blot analysis of human-mouse somatic cell hybrids (Shows, T. B, et al., Adv. Hum. Genet. 12: 341-452 (1982)). The presence or absence of fragments detected by the G8 probe was determined for 18 karyotyped hybrids (Table 1). These fragments were always seen when chromosome 4 was present in the hybrid cell line, but never seen when chromosome 4 was absent. For all other chromosomes, there were several discordant clones. Seven of the hybrids were tested using the enzyme Hind III, while the rest were monitored after EcoR I digestion. In both cases, all fragments detected in total genomic DNA co-segregated with chromosome 4.

ues in the Venezuela population might vary from these estimates. Results of the analysis for G8 and Huntington's Disease, together with those for two other chromosome 4 markers are given in Table 2.

TABLE 1

Segregation of G-8 with Human Chromosomes in Human-Mouse Hybrids

| Cell Hybrid | G-8 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Translocated Chromosomes |
|---|---|---|---|---|---|---|---|---|---|---|---|---|---|---|---|---|---|---|---|---|---|---|---|---|---|
| WIL-5 | + | − | − | − | + | − | − | − | − | − | − | − | − | − | − | − | − | − | + | + | − | − | + | − | + | |
| WIL-2 | − | − | − | − | − | − | − | − | + | − | − | − | + | − | − | − | − | − | + | − | − | − | + | − | + | |
| WIL-7 | − | − | + | + | − | + | + | + | − | − | + | + | − | + | + | − | − | − | + | + | − | − | + | + | − | |
| JSR-22H | + | − | − | − | + | − | + | − | − | − | + | + | − | − | + | − | − | − | + | + | − | + | + | − | − | 2/1 |
| XTR-22 | + | − | + | − | + | + | + | − | + | − | + | + | − | − | − | − | − | − | + | + | + | + | + | − | X/3 |
| TSL-2 | − | − | + | − | − | + | + | − | − | − | + | − | + | − | − | − | − | − | + | − | + | + | − | + | 17/3 |
| JSR-17S | − | − | + | − | − | + | + | − | − | − | + | − | + | − | − | − | − | − | − | − | + | + | + | − | 7q− |
| ATR-13 | + | + | + | + | + | + | + | + | + | − | + | − | + | + | + | + | + | + | + | + | − | − | − | − | 5/X |
| WIL-6 | + | − | − | − | + | + | + | + | + | − | + | + | − | − | + | − | − | + | − | + | + | + | − | + | |
| NSL-5 | − | − | − | − | − | − | − | − | − | − | + | − | + | + | + | − | + | − | + | − | − | − | − | 17/9 |
| NSL-9 | − | − | − | − | − | + | − | + | − | + | + | + | + | + | + | − | − | + | + | + | − | |
| NSL-15 | + | − | + | − | + | + | − | + | + | − | − | − | + | + | + | − | + | + | + | − | + | + | + | |
| NSL-16 | + | − | − | + | + | + | − | + | − | − | − | − | + | − | − | − | − | + | + | − | − | + | − | + | 17/9 9/17 |
| REW-5 | + | + | + | + | + | + | + | + | + | + | + | + | + | + | − | + | − | + | + | + | − | + | + | + | |
| REW-7 | + | + | + | + | + | + | + | + | + | − | + | + | + | + | − | + | + | + | + | + | + | + | + | |
| REW-10 | − | − | + | + | − | + | + | + | + | + | + | + | + | + | + | + | + | + | + | + | − | + | |
| REW-11 | − | − | − | − | − | − | − | − | − | − | + | − | + | − | − | + | − | − | − | + | + | − | + | |
| JWR-26C | + | − | + | + | + | + | + | + | − | + | + | + | + | − | + | + | + | + | − | + | + | − | + | 1p− |
| % Discordancy* 28 hybrids | | 38 | 31 | 38 | 7Y | 35 | 37 | 30 | 32 | 38 | 46 | 32 | 54 | 46 | 43 | 48 | 50 | 57 | 26 | 50 | 50 | 44 | 36 | 32 |

Footnotes:
DNA was isolated from an aliquot of cells at the same passage that karyotypic and enzyme analyses were performed. The presence of G8 sequences was determined by hybridization of the probe to filters containing Hind III-digested (first seven hybrids) or EcoR I-digested (remaining hybrids) cell hybrid DNA. Under the hybridization conditions used G8 did not detect hybridizing fragments in mouse DNA. A hybrid cell was considered positive for a given human chromosome only if it was present in greater than 10% of the cells. Some hybrids were made from fibroblasts containing the following translocation chromosomes: ATR-5/X, (5pter→5q35:22→Xqter); JSR-7q, (7pter→7q33); NSL-17/9, (17qter→17p11::9qter); 9/19, (9pter→9q12::17p11→17pter); JSR-2/1, (2pter→2q37::1p21 1pter); 1p−, (1qter→1p21::2q37→2pter); TSL-3/17, (3qter→3p21::17p13→17pter); XTR-X/3, (Xpter→Xq28::3q21→3qter).
*Twenty-eight additional hybrid cells were analysed for their chromosome content using only marker enzymes previously assigned to each human chromosome. The references for the gene assignments and assay methods are given in Shows, et al., supra. The markers tested are: chromosome 1, adenylate kinase-2, peptidase-C; 2, malate dehydrogenase (soluble), isocitrate dehydrogenase (soluble); 3, aminoacylase-1, DNA segment (D3S1); 4,peptidase S; 5,hexosaminidase B; 6, malic enzyme, superoxide dismutase (mitochondrial); 7,phosphoserine phosphatase, beta-glucuronidase; 8,glutathione reductase; 9, adenylate kinase-1, aconitase (soluble); 10,glutamate-oxaloacetate transaminase; 11, esterase-A4, lactate dehydrogenase-A; 12, lactate dehydrogenase-B, peptidase-B; 13,esterase-D; 14, nucleoside phosphorylase; 15, mannose phosphate isomerase, pyruvate kinase (muscle form); 16, adenine phosphoribosyl transferase; 17, galactokinase; 18, peptidase-A; 19, glucose phosphate isomerase, peptidase-D; 20, adenosine deaminase; 21, superoxide dismutase (soluble); aconitase (mitochondria), DNA segment (D22S1); X, glucose-6-phosphate dehydrogenase, phosphoglycerate kinase.
YThe two discordant clones were positive for G8 and negative for peptidase-S. These discordancies are probably due to the greater sensitivity of Southern blot hybridization to the peptidase-S stain.

An additional 28 hybrids were tested only for enzyme markers previously assigned to each of the human chromosomes. Two discordant clones were seen with the chromosome 4 marker peptidase S, probably due to the relative insensitivity of the peptidase S assay compared to Southern blot hybridization. A much higher rate of discordance (>26%) was seen for all other human chromosomes. These data clearly assign the fragments detected by G8 to chromosome 4. The G8 DNA segment was recently given the designation D4S10 at The Human Gene Mapping Workshop 7.

Analysis of Linkage

After initial data were obtained for the American Huntington's Disease family, selected members of the Venezuela family were typed using marker G8. The haplotypes observed in these families are displayed in FIGS. 3 and 4. The data were analyzed for linkage of the DNA marker to the Huntington's Disease gene using the program LIPED. At-risk individuals included in the analysis were assigned a probability of having inherited the gene based on an age of onset function as previously described (Pericak-Vance, supra). The cumulative distribution of age of onset was assumed to be similar in the American and Venezuelan families. Haplotype frequencies used for the G8 marker were those predicted from the individual allele frequencies for the site 1 and site 2 RFLP's assuming complete equilibrium. It should be noted that these frequencies were observed in the North American population and their exact val-

TABLE 2

| | | Lod Scores | | | | | |
|---|---|---|---|---|---|---|---|
| | | Recombination fraction ($\theta$) | | | | | |
| | | 0.0 | 0.05 | 0.1 | 0.2 | 0.3 | 0.4 |
| Huntington's Disease against G8 | A | 1.81 | 1.59 | 1.36 | 0.90 | 0.48 | 0.16 |
| | V | 6.72 | 5.96 | 5.16 | 3.46 | 1.71 | 0.33 |
| | T | 8.53 | 7.55 | 6.52 | 4.36 | 2.19 | 0.49 |
| Huntington's Disease against MNS | | $-\infty$ | −3.22 | −1.70 | −0.43 | −0.01 | 0.49 |
| Huntington's Disease againgst GC | | $-\infty$ | −2.27 | −1.20 | −0.32 | 0.00 | 0.07 |
| G8 against MNS | | $-\infty$ | −8.38 | −3.97 | −0.55 | 0.45 | 0.37 |
| G8 against GC | | $-\infty$ | −2.73 | −1.17 | −0.08 | 0.14 | 0.08 |

The maximum lod score for Huntington's Disease against G8 was 8.53 at a $\theta$ of 0.00, suggesting that the two loci are very closely linked. The maximum lod score was obtained at a $\theta$ of 0.00 for both sexes. No recombinants can be detected in either pedigree. The Huntington's Disease gene segregated with the A haplotype of G8 in the American family and with the C in the Venezuela pedigree.

A 99% confidence interval (in this case one-sided) for the distance between the Huntington's Disease locus and G8 is computed as the value of $\theta$ at which the likelihood is 100 times less than its maximum value, that is 2 log units less than 8.53. The lod score at 10 centimorgans (cM) is 6.52. Thus, the 99% confidence interval is 0–10 centimorgans. One can also obtain a confidence interval based on the total number of non-crossovers. However, in these Huntington's Disease pedigrees, this approach is not feasible because at-risk individuals cannot be determined as crossovers.

The lod scores for both Huntington's Disease and G8 against MNS (located between 4q28 and 4q31) and GC (located between 4q11 and 4q13) suggest that these latter markers are not close to either the Huntington's Disease or G8 locus. These results eliminate a substantial portion of chromosome 4 as the possible region containing the Huntington's Disease gene.

Having now fully described this invention, it will be understood that the same can be carried out within a broad and equivalent range of probes, conditions, enzymes, detection techniques, and the like without affecting the spirit or scope of the invention or of any embodiment herein.

What is new and is intended to be covered by Letters Patent of the United States is:

1. A method for detecting the presence in a subject of the gene for Huntington's Disease which comprises:
analyzing the human chromosome 4 of said subject for a DNA polymorphism linked to Huntington's Disease.

2. The method of claim 1 wherein said polymorphism is a restriction fragment length polymorphism (RFLP).

3. The method of claim 2 wherein said step of claim 2 wherein said step of analyzing is carried out by:

(a) digesting DNA from said subject with a restriction endonuclease enzyme;
    (b) separating fragments obtained from said digestion;
    (c) detecting said RFLP with a hybridization probe containing sequence information capable of hybridizing to and identifying said RFLP, thereby generating a restriction pattern; and
    (d) correlating the presence or absence of said RFLP in said digest with the respective presence or absence of the Huntington's Disease gene.

4. The method of claim 3 wherein said probe is detectably labelled.

5. The method of claim 3 wherein at least two different digestions with two different restriction endonuclease enzymes are carried out.

6. The method of claim 3 wherein several probes are utilized to detect several RFLP's.

7. The method of claim 3 wherein the restriction pattern for said subject is compared with the corresponding restriction pattern for family members showing segregation between the Huntington's Disease gene and said RFLP.

8. The method of claim 7 wherein the restriction pattern for said subject is compared to the corresponding restriction pattern for a parent of said subject which is unaffected by Huntington's Disease, a parent of said subject which is affected by Huntington's Disease and sibling of said subject which is affected by Huntington's Disease.

9. The method of claim 3 wherein said probe is radiolabelled G8.

10. The method of claim 3 wherein said separation is by agarose gel electrophoresis.

* * * * *